US006746438B1

(12) United States Patent
Arnissolle

(10) Patent No.: US 6,746,438 B1
(45) Date of Patent: Jun. 8, 2004

(54) DEVICE FOR TWO-WAY TRANSFER OF A LIQUID BETWEEN A BOTTLE AND A CARTRIDGE

(75) Inventor: Yves Arnissolle, St Genis Laval (FR)

(73) Assignee: Sedat, Irigny (DE)

( * ) Notice: Subject to any disclaimer, the term of this patent is extended or adjusted under 35 U.S.C. 154(b) by 307 days.

(21) Appl. No.: 09/913,537

(22) PCT Filed: Mar. 17, 2000

(86) PCT No.: PCT/FR00/00671

§ 371 (c)(1),
(2), (4) Date: Aug. 15, 2001

(87) PCT Pub. No.: WO00/54723

PCT Pub. Date: Sep. 21, 2000

(30) Foreign Application Priority Data

Mar. 18, 1999 (FR) ........................................... 99 03392

(51) Int. Cl.$^{7}$ ................................................ A61B 5/32
(52) U.S. Cl. ....................... 604/411; 604/905; 604/533
(58) Field of Search ................................ 604/181, 533, 604/198, 263, 905, 408–415, 244, 83, 86, 192, 199, 256, 239, 264, 272, 537, 538; 141/329, 369, 370, 374, 382, 383

(56) References Cited

U.S. PATENT DOCUMENTS 3,490,437 A 1/1970 Bakondy
3,563,373 A * 2/1971 Paulson .................... 206/63.2
4,191,225 A 3/1980 Ogle
4,259,956 A 4/1981 Ogle
4,791,466 A 12/1988 Kato
5,603,695 A 2/1997 Erickson

FOREIGN PATENT DOCUMENTS

CH 676548 A5 * 4/1988
CH 676 548 A5 2/1991

* cited by examiner

*Primary Examiner*—Manuel Mendez
(74) *Attorney, Agent, or Firm*—Sughrue Mion, PLLC

(57) ABSTRACT

The invention concerns a device for the two-way transfer of a liquid (38) between a bottle (14) provided with a cap (44) capable of being perforated at a cartridge (12) comprising a cylindrical reservoir (26) wherein slides a piston (34) capable of being perforated. It comprises: a body (16) including means to be fixed on the bottle (14); a member (24) linking the piston (34) capable of being perforated to the body (16); a shuttle (20) relative to the body (16) and said linking member (24), the shuttle bearing a hollow needle (22) whereof one first end (112) is adapted to pierce the piston (34) and whereof the second end (114) is adapted to pierce the cap (44). The shuttle (20) is mobile between a piston wherein the needle ends (112, 114) are spaced apart from the piston (34) capable of being perforated and the cap (44) capable of being perforated and an end-of-stroke transferring position wherein the needle ends (112, 114) are received in the cartridge (12) and the bottle (14).

10 Claims, 5 Drawing Sheets

DEVICE FOR TWO-WAY TRANSFER OF A LIQUID BETWEEN A BOTTLE AND A CARTRIDGE

BACKGROUND OF THE INVENTION

The present invention relates to a device for two-way transfer of a liquid between a bottle, provided with a perforable stopper, and a cartridge, comprising a cylindrical reservoir in which a perforable piston slides.

Before proceeding with an injection using a syringe, it is common for the practitioner to have to mix the liquid contained initially in the syringe with a lyophilisate which is contained initially in a bottle provided with a perforable stopper.

To mix these extemporaneously, the practitioner first injects all of the liquid contained in the syringe into the bottle. To this end, he perforates the stopper of the bottle with the aid of the needle which is provided on the syringe and is intended for the injection proper.

After the lyophilisate has dissolved in the liquid, the mixture obtained is reaspirated into the syringe through the injection needle. After the needle has been removed from the bottle, the injection proper on the patient is carried out.

Carrying out this extemporaneous mixing using such means is relatively awkward, and it also poses the risk of the injection needle being contaminated upon its introduction into the bottle.

Devices are also known for transferring fluid between a bottle and a flexible bag intended in particular for transfusion. However, these devices are not designed to permit two-way transfer of a liquid between a bottle and a syringe.

SUMMARY OF THE INVENTION

It is an object of the invention to make available a solution to the problem of two-way transfer of a liquid between a bottle and an injection syringe by making available a device which is easy to use and which guarantees satisfactory aseptic conditions.

To this end, the subject of the invention is a device for two-way transfer of a liquid between a bottle, provided with a perforable stopper, and a cartridge, comprising a cylindrical reservoir in which a perforable piston slides, characterized in that it includes a body having means for fixing to the bottle, a member for connecting the perforable piston to the body, and a shuttle which is displaceable relative to the body and to said connecting member, the shuttle bearing a hollow needle of which a first end is adapted to perforate the piston and of which the second end is adapted to perforate the stopper, and in that the shuttle is displaceable between an initial position, in which the needle ends are spaced apart from the perforable piston and the perforable stopper, and a final transfer position, in which the needle ends are received in the cartridge and the bottle.

According to particular embodiments, the transfer device includes one or more of the following characteristics:

- said member for connecting the piston to the body comprises means for fixing to the body and is movable relative to the body from an initial position, in which the fixing means are not in engagement with the body, and a final position, in which the fixing means are in engagement with the body, thus ensuring that the piston is connected to the body;
- said member for connecting the piston to the body comprises a threaded protuberance for fixing it in a tapped recess in the piston;
- said shuttle is mounted so as to slide in a conduit of said member for connecting the piston to the body;
- said conduit has on the inside an abutment limiting the displacement travel of the shuttle;
- it comprises a protective cap initially mounted on the body, which protective cap has means for fixing it to the reservoir of the cartridge;
- the body has a continuation surrounding said shuttle and extending beyond the first end of the needle;
- it comprises at least one abutment limiting the axial displacement of the reservoir relative to the connecting member, preventing removal of the piston from the reservoir; and
- it comprises a cartridge support on which the reservoir of the cartridge bears axially, and in that one of the cartridge support and connecting member has at least one projection, forming said abutment, received in a longitudinal slit of the other of the cartridge support and connecting member, in order to limit their relative axial displacement between the reservoir and the connecting member.

The invention also relates to an injection kit including a device for two-way transfer as defined above, and a cartridge and a bottle, in which the cartridge is initially connected to the attachment member and the bottle is initially connected to the body.

BRIEF DESCRIPTION OF THE DRAWINGS

The invention will be better understood on reading the following description which is given solely by way of example and in which reference is made to the drawings, in which.

DETAILED DESCRIPTION OF THE INVENTION

Figure 1:
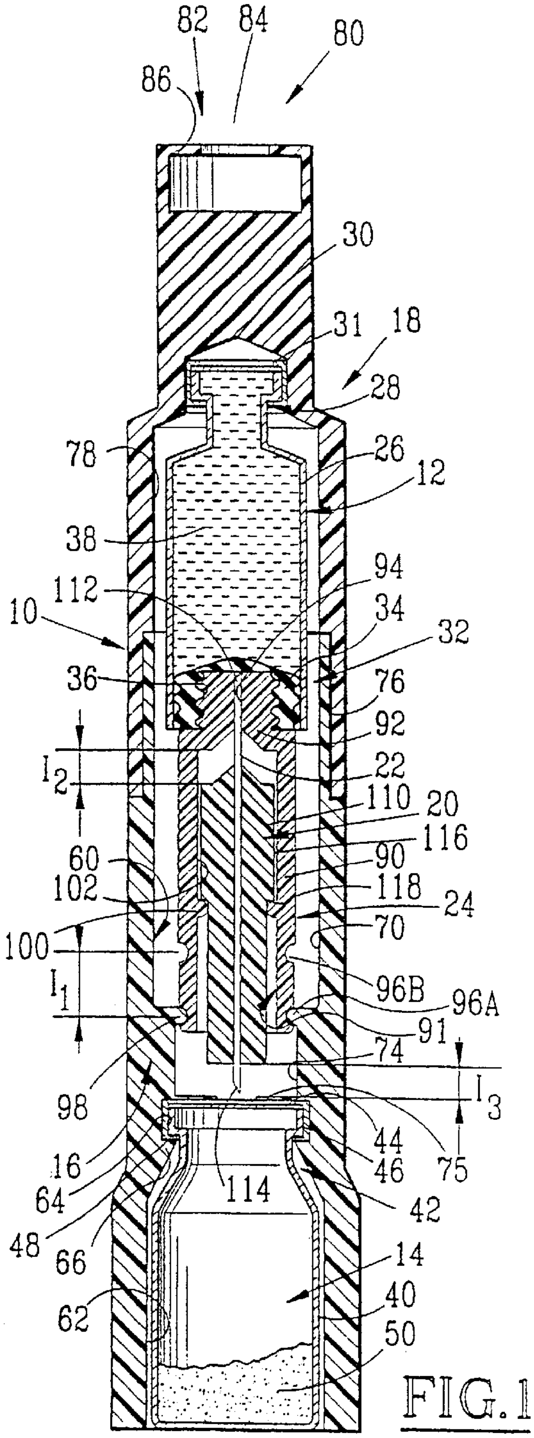
FIG. 1 is a longitudinal cross-sectional view of the transfer device according to the invention in its storage position.

The transfer device 10 shown in FIG. 1 is designed for two-way transfer of fluid bet ween a cartridge 12 and a bottle 14. This device is generally of revolution about its longitudinal axis. It mainly comprises a body 16, a protective cap 18, a shuttle 20 bearing a hollow needle 22, and a screw pusher or connecting member 24 intended to ensure axial securing of the movable piston of the cartridge 12 and the body 16.

In FIG. 1, the transfer device 10, equipped with the cartridge 12 and the bottle 14, is shown in its storage position before use.

The cartridge 12 is intended for carrying out an injection after it has been withdrawn from the transfer device and is equipped with an injection needle and an actuating pusher. It comprises a cylindrical reservoir 26 which at the front has a narrowed neck 28 closed off by a perforable cap 30 supported by an a head 31. The cap 30 is designed to be perforated by an injection needle mounted on the head 31 of the cartridge with a view to proceeding with an injection.

The rear end 32 of the reservoir 26, at the opposite end from the head 31, is closed of by a perforable piston 34 mounted so as to slide in a leaktight manner inside the reservoir 26. The piston 34 has axially a recess 36 opening to the outside of the cartridge. This recess is tapped internally in order subsequently to allow screwed insertion of an actuating pusher with a view to injecting the liquid contained in the cartridge.

The piston 34 is made of a polymer material of given Shore hardness.

The cartridge 12 is initially filled with an injectable liquid 38.

The bottle 14 comprises a glass body 40 with a neck 42 closed off by a perforable stopper 44. The neck 42 has a peripheral rim 46 defining a shoulder 48.

The perforable stopper 44 is made of a polymer material having substantially the same Shore hardness as the material from which the piston 34 is made. Thus, the piston 34 and the stopper 44 have the same resistance to engagement of a sharp point. The materials from which the stopper 44 and the piston 34 are made are advantageously the same. Moreover, their thicknesses measured on the axis X—X are substantially identical.

The bottle 14 is initially filled with a lyophilisate 50 constituting a medicinal substance in powder form. The oyophilisate 50 only partially fills the bottle. As is known per se, the bottle is sealed under vacuum so that the pressure inside the bottle is very much lower than the atmospheric pressure.

The body 16 has a conduit 60 passing axially through it from one end to the other. At one end, called the lower end, the conduit 60 defines a seat 62 for receiving the bottle. This seat has a countersink 64 for receiving the rim 46 of the bottle 14 in order to fix the latter. In particular, the countersink 64 is delimited by projections 66 defining profiles for fixing the bottle. They are designed to cooperate with the shoulder 48 delimited by the neck of the bottle. The projections 66 have ramps converging from the open end of the seat 62 so as to make it easier to introduce the bottle into the body.

At its other end, called the upper end, the conduit 60 has a cylindrical chamber 70 in which the shuttle 20 and the connecting member 24 are received. The chambers 62 and 70 are linked via an intermediate portion 74 of smaller diameter.

The chamber 70 has a diameter which is sufficient to allow the passage of the reservoir 26. The total length of the chamber 70 and of the portion 74 is advantageously greater than that of the hollow needle 22.

The portion 74 is partially closed, at its end which opens into the chamber 62, by a membrane 75 which delimits an opening sufficient for the passage of the needle 22. This membrane 75 partially covers the membrane 44 of the bottle 14.

At its upper end, the body 16 has on the outside a shoulder 76 reducing the thickness of the body. This is designed for fitting the protective cap 18.

The protective cap 18 generally has the form of a sleeve and defines a seat 78 which is able to receive the cartridge 16 and to be engaged from its open end partially about the body 16.

It additionally comprises, on the outside, at its blind end, means 80 for fixing on the head 31 of the cartridge. As is shown in perspective in FIG. 3, the means 80 comprise a fork 82 delimited by two arms which define a notch 84 which extends radially and whose width corresponds to the diameter of the narrowed neck 28. Behind the fork 82, a chamber 86 is provided in the protective cap 80 for the purpose of receiving the head 31.

The connecting member 24 has a tubular shape. It comprises a cylindrical side wall 90 delimiting a conduit 91. It is closed off at an upper end by a threaded protuberance 92 projecting outward. This protuberance 92 is screwed inside the tapped recess 36 and thus ensures that the connecting member 24 and the piston 34 are axially secured.

The protuberance 92 is provided with an axial conduit 94 whose diameter corresponds substantially to the external diameter of the needle 22.

At its lower end, the connecting member 24 has, on the outer surface of its wall 90, two successive grooves 96A, 96B which are spaced axially apart. They are separated by a distance $I_1$. The grooves 96A and 96B are designed to cooperate with a peripheral flange 98 formed in the conduit 60 of the body. The flange is provided at the end of the intermediate portion 74 opening into the chamber 70.

The groove 96 and the peripheral flange 98 are designed to secure the connecting member 24 and the body 16. The flange 98 is initially engaged in the lower groove 96A.

The distance $I_1$ is chosen to be smaller than the length of the intermediate portion 74, less the thickness of the membrane 75.

The wall 90 of the connecting member 24 has on the inside a peripheral flange 100 which delimits, in the space circumscribed by the wall 90, a chamber 102 confining the shuttle 20. Thus, the flange 100 forms an axial abutment for stopping the shuttle 20.

The shuttle 20 is made up of a cylindrical slide 110, with the hollow needle 22 passing axially through the latter from one end to the other. Thus, a first end 112 of the needle protrudes beyond the slide 110 and is received initially in the passage 94. The second end 114 of the needle 22 protrudes rearward of the slide 110 and is initially arranged facing the stopper 44 of the bottle.

The two ends of the needles have analogous bevels, so that they have sharp points with the same profiles facing the piston 34 and the stopper 44.

The diameter of the slide 110 is greater than the diameter of the passage defined by the membrane 75.

The cylindrical slide 110 has, along a part of its length received in the confinement chamber 102, longitudinal ribs 116 (FIG. 3) which define a shoulder 118 which is designed to cooperate with the peripheral flange 11 forming an abutment. The longitudinal ribs 116 guide the shuttle 20 in translation inside the connecting member 24.

The length of the ribs 116 is smaller than the length of the confinement chamber 112 defined between the protuberance 92 and the flange 100. This difference in length is labeled $I_2$.

Initially, as is shown in FIG. 1, the connecting member 24 is free from the body 16, so that the fixing means formed by the groove 96A and the flange 98 are in engagement. Likewise, the shuttle 20 initially bears on the peripheral flange 100 by way of the shoulder 118, so that the end 112 of the needle extends inside the protuberance 92. It is thus spaced apart from the perforable piston 34. The shuttle is then spaced apart by the distance $I_2$ from the protuberance 92.

Likewise, the end 114 of the hollow needle is kept spaced apart from the stopper 44 by the lower end of the connecting member 24 bearing on the peripheral flange 98 and the shuttle 20 bearing on the flange 100. The lower end of the slide 11 is then separated from the stopper 44 by a distance $I_3$.

The distances $I_1$, $I_2$ and $I_3$ are advantageously related to each other such that $I_1=I_2+I_3$.

The transfer devise 10 is used in the following way.

Figure 2:
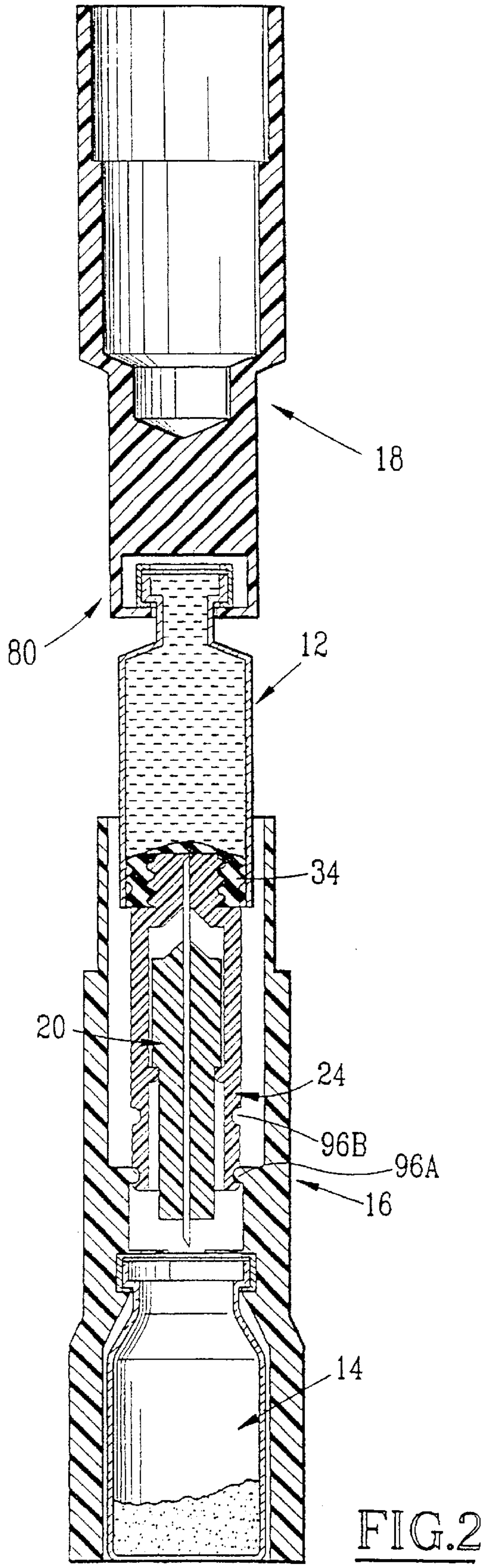
FIGS. 2 and 3 are a longitudinal cross-sectional view and a perspective and partially cutaway view, respectively, of the transfer device in its initial phase of use.
Figure 3:
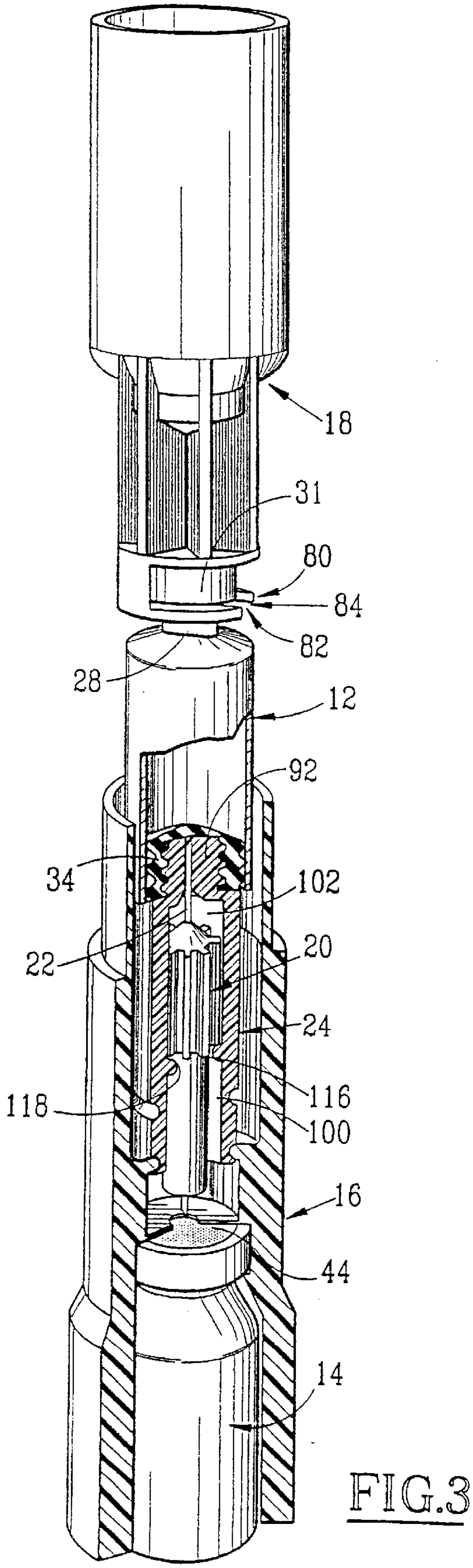

The protective cap 18 is first pulled off and turned. The fixing means 80 are engaged about the head 31 of the cartridge, as is shown in FIGS. 2 and 3.

Figure 4:
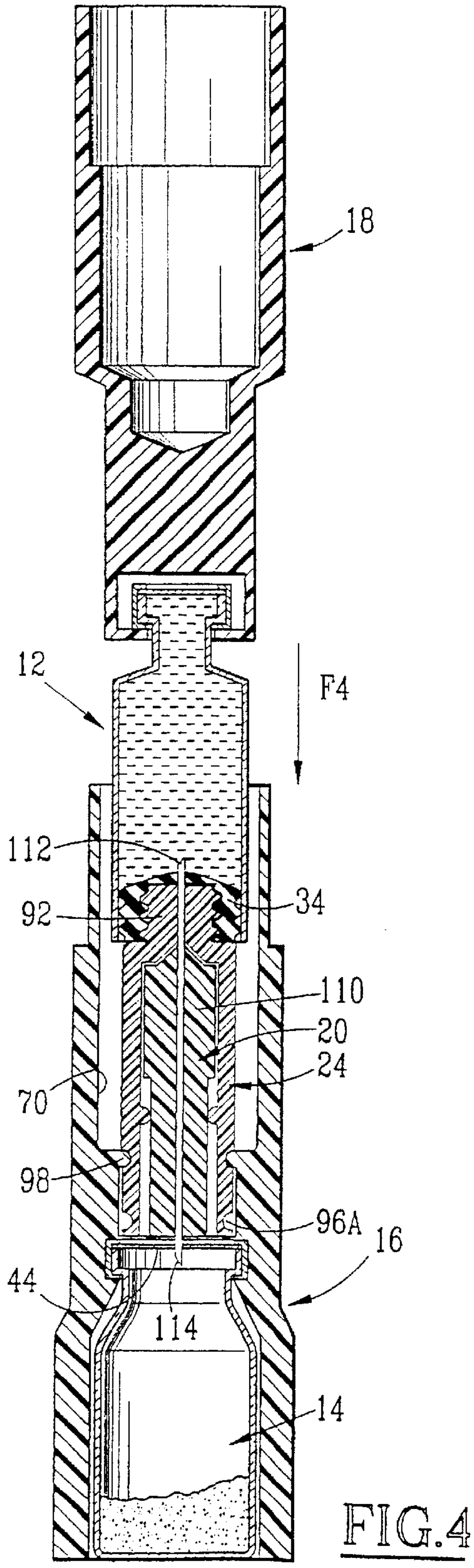
FIG. 4 is a longitudinal cross-sectional view of the transfer device after the needle ends have penetrated into the bottle and the cartridge.

The protective cap 18 and the body 16 are then moved together in the direction of the arrow F4, as is shown in FIG. 4. Upon this axial displacement, the shuttle 20 moves relative to the body 16 until a transfer position is reached in which the end 112 protrudes inside the cartridge 12 after passing through the piston 34 and the end 114 protrudes inside the bottle 14 after passing through the stopper 44.

The displacement of the protective cap 18 in fact brings about the engagement of the cartridge 12 in the chamber 70 of the body. Upon this displacement, the connecting member 24 is displaced toward the bottle 14 by being pushed by the cartridge. The groove 96A disengages from the peripheral flange 98 and the lower end of the member 24 is displaced until the flange 98 is received in the peripheral groove 96B. The elastic engagement of the flange 98 in the groove 96B ensures definitive axial securing of the connecting member 24 and the body 16.

Upon displacement of the connecting member 24 along the course $I_1$, the shuttle 20, mounted so as to slide inside the connecting member 24 along a course of length $I_2$, is also displaced relative to the body 16 and the member 24.

In fact, at the start of the sliding of the connecting member 24, the ends 112 and 114 of the needle come to bear respectively on the piston 34 and the stopper 44. These latter then perforate the piston 34 and the stopper 44 simultaneously as the cartridge 12 and the bottle 14 are brought together. The ends of the needle then penetrate into the cartridge 12 and the bottle 14.

As the Shore hardness values for the piston 34 and for the stopper 44 are identical, and likewise the two profiles of the ends 112 and 114 of the needle, the initial perforations of the piston and of the membrane are effected simultaneously, the needle being stressed only at these two ends.

At the end of displacement of the connecting member 24, the slide 110 comes into abutment, on the one hand, on the end protuberance 92 of the connecting member and, on the other hand, against the membrane 75 extending over the stopper 44 which closes the bottle. In this position, shown in FIG. 4, the hollow needle 22 ensures communication between the bottle 14 and the cartridge 12.

Figure 5:
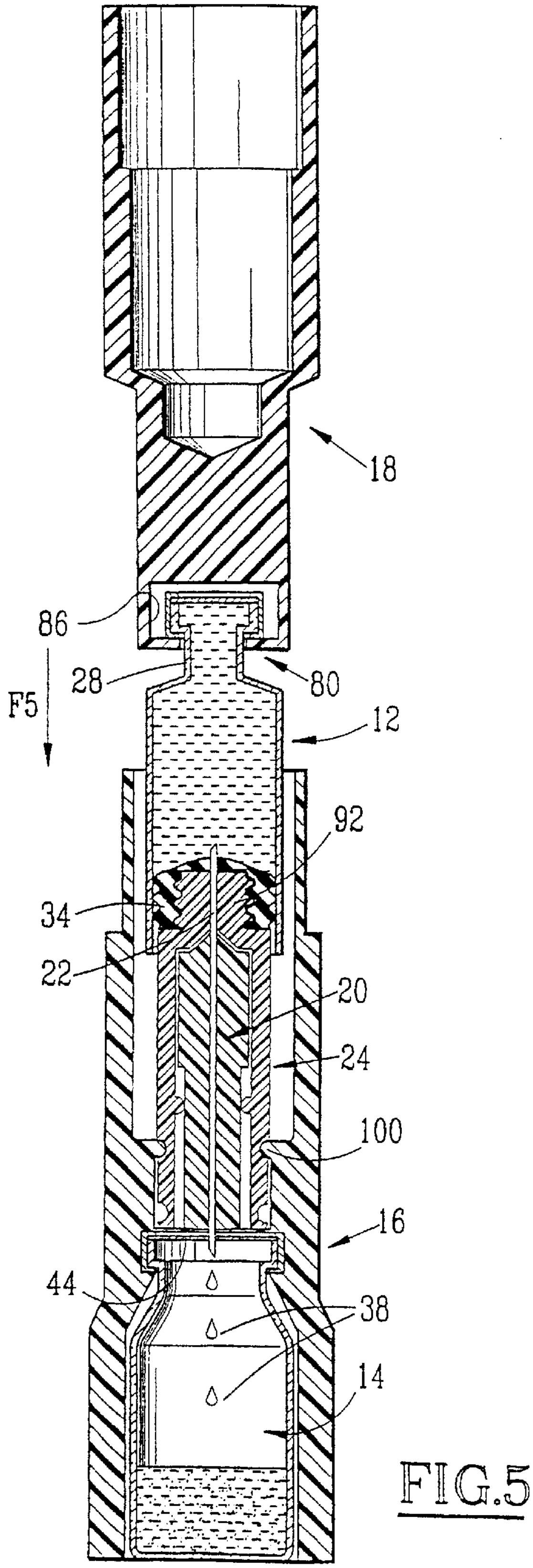
FIG. 5 is a longitudinal cross-sectional view of the transfer device during the phase of transfer of the fluid from the cartridge to the bottle.

As is illustrated in FIG. 5, when the reservoir 26 is subsequently engaged in the body 16 under the action of the protective cap 18 displaced toward the body 16 in the direction of the arrow F5, the liquid 38 initially contained in the cartridge 12 is gradually transferred into the bottle 14.

This transfer results from the engagement of the piston 34 inside the cylindrical reservoir 26, the piston 34 being held fixed in relation to the body by way of the connecting member 24 which thus forms an abutment while the reservoir 26 is displaced toward the body 16.

Filling the bottle 14 is made possible because it is initially at a pressure below atmospheric pressure.

Figure 6:
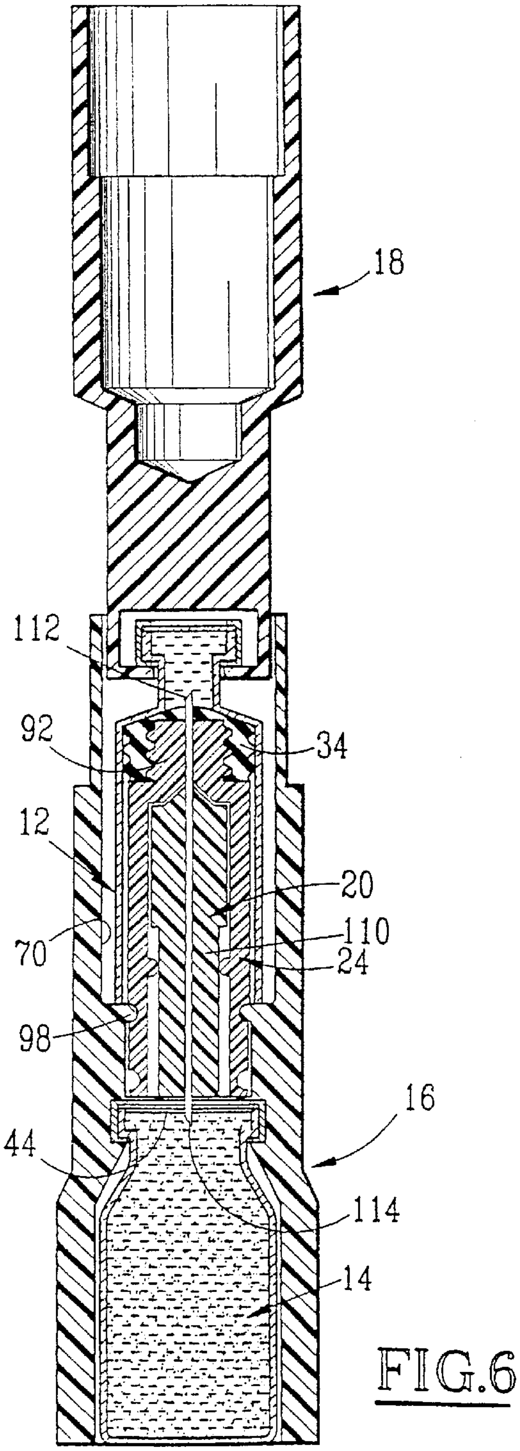
FIG. 6 is a longitudinal cross-sectional view of the transfer device once all the liquid has been transferred to the bottle.

When, as is shown in FIG. 6, the piston 34 is bearing against the neck 28 of the cartridge, most of the liquid initially contained in it is transferred into the bottle 14.

After sufficient shaking, the lyophilisate 50 dissolves in the liquid 38 inside the bottle 14.

Figure 7:
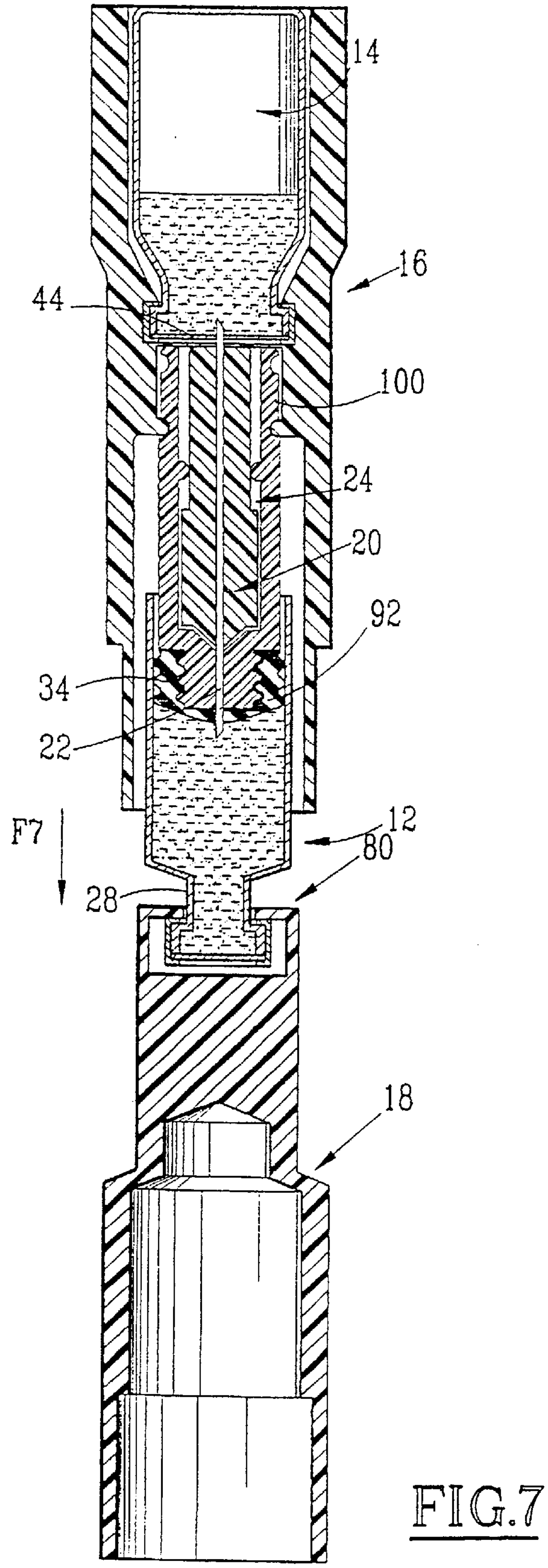
FIG. 7 is a longitudinal cross-sectional view of the transfer device when returning the mixture from the bottle to the cartridge.

To transfer the extemporaneous mixture thus formed to the inside of the cartridge 12, the transfer device 10 is turned around, as is shown in FIG. 7, then the protective cap 18 is removed from the body 16 and the extemporaneous mixture is aspirated into the cartridge.

During the pull exerted on the cylindrical reservoir 26 of the cartridge in the direction of the arrow F7, the piston 34 is kept integral with the body 16 by way of the connecting member 24 fixed to the body through the cooperation of the groove 96B and the peripheral flange 98.

The mixture is aspirated under the action of the movement of the cylindrical reservoir 26 relative to the piston 34. The relative movement of the piston and of the reservoir in fact creates an underpressure inside it, which leads to aspiration of the mixture contained in the bottle 14.

After the cartridge 12 has been filled completely with the extemporaneous mixture, the cartridge 12 is detached from the connecting member 24 by being unscrewed. It can then be used for injection purposes after being fitted with an injection needle and an actuating pusher.

The transfer device thus without the cartridge is then discarded. It should be noted that in this position the end 112 of the needle is protected on account of the continuation of the body 16, thereby avoiding any risk of accidental needle stick injuries. To this end, the length of the body 16 is chosen to be sufficient to continue beyond the end 112 of the hollow needle.

The device according to the invention permits a transfer of the liquid between the cartridge and the bottle without any risk of contamination of the liquid. This is because the two ends of the hollow needle are at all times protected inside the closed space delimited by the connecting member 24, the body 16 and the bottle 14.

This protection is further reinforced by the presence of the protective cap 18 during storage of the device.

Moreover, the simultaneous penetration of the two ends of the needles avoids any risk of ambient air entering the cartridge or the bottle.

When the transfer device is pre-fitted with a bottle 14 and a cartridge 12 before delivery, the transfer can be carried out without any need for the cartridge or the bottle to come back into contact with the hand. This eliminates any risk of contamination from the hands.

Figure 8:
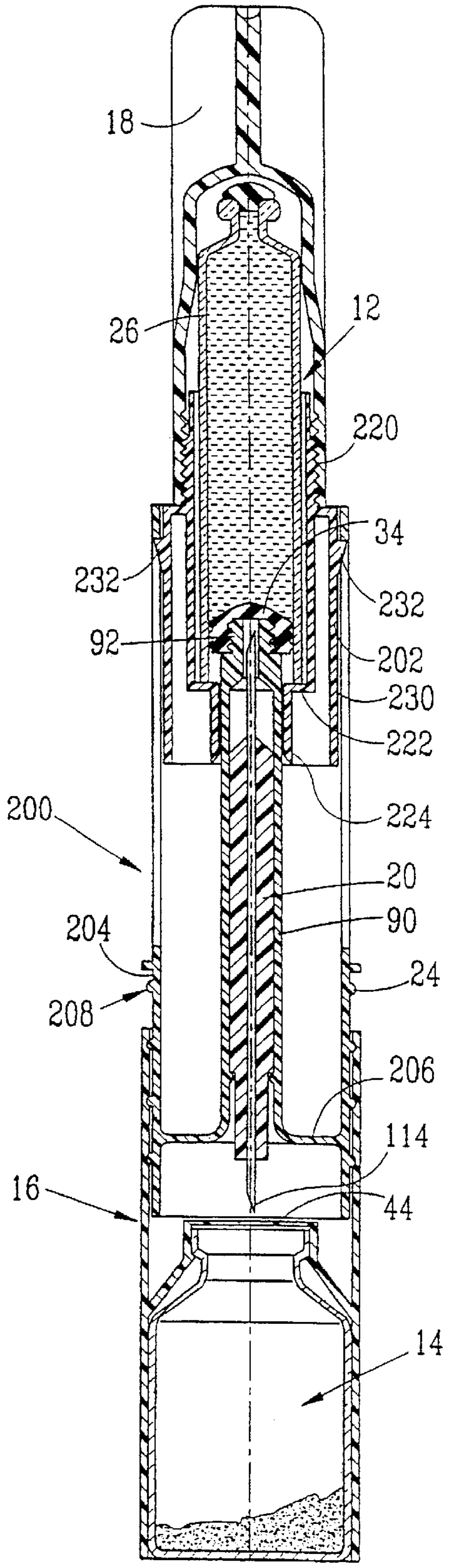
FIG. 8 is a cross-sectional view of an alternative embodiment of the transfer device according to the invention.
Figure 9:
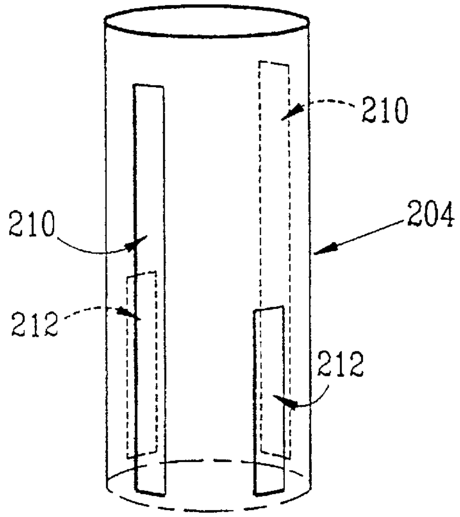
FIG. 9 is a partial perspective view of the connecting member of the device in FIG. 8.

An alternative embodiment of the transfer device according to the invention is shown in FIGS. 8 and 9. In this figure, the elements which are analogous or identical to those of the embodiment in FIGS. 1 through 7 are designated by the same reference numbers.

This figure shows a transfer device 200 combined with a cartridge 12 and a bottle 14 containing a lyophilisate.

The transfer device 200 comprises a body 16 in which the bottle 14 is axially immobilized, a connecting member 24 which slides relative to the body, and a needle-holedr shuttle 20 which slides freely along the axis of the connecting member 24.

The transfer device 200 additionally comprises a cartridge support 202 which has means 203 for axially fixing the cap 18.

In this embodiment, the connecting member 24 includes, in addition to the cylindrical wall 90, a coaxial outer sleeve 204 which surrounds the cylindrical wall 90 and is connected to it by an annular wall 206. The sleeve 204 is mounted so as to slide inside the body 16. It has raised and recessed profiles 208 designed to cooperate with complementary profiles provided on the side wall of the body 16 in order to axially secure these after perforation of the stopper 44 by the end 114 of the hollow needle.

The sleeve 204 continues beyond the threaded protuberance 92 screwed into the piston 34 of the cartridge.

As is shown in FIG. 9, the sleeve 204 has, in its side wall, two pairs of longitudinal slits 210, 212 offset by an angle of 90°. The slits 210 have a length twice that of the slits 212. The lower end of the two pairs of slits 210, 212, arranged toward the bottle 14, extend at the same level on the sleeve 204.

The cartridge support 202 comprises an inner tube 220 for receiving the body 26 of the cartridge. It is partially closed at its lower end by a shoulder 222 on which the open end of the reservoir 26 of the cartridge bears axially. The shoulder 222 is continued by a tubular portion 224 sliding along the cylindrical wall 90 of the connecting member. In addition, the tube 220 is surrounded in its lower part by a coaxial sleeve 230 bearing two diametrically opposite projections 232 which are designed to slide inside one or other of the pair of slits 210, 212.

Depending on the capacity of the cartridge 12 used with the transfer device, the projections 232 are introduced into one or other of the pairs of slits. For a cartridge with a capacity of 1.3 mm, that is to say a cartridge having a body of reduced length, the projections 232 are arranged in the short slits 212.

By contrast, when the transfer device is used with a cartridge having a capacity of 2.3 ml, that is to say a cartridge in which the length of the body is twice that of a cartridge of 1.3 ml, the projections 232 are engaged in the slits 210.

It will be appreciated that the cartridge support 202 guides the cartridge 12 axially as it slides relative to the connecting member 24. The presence of the two pairs of slits on the sleeve 204 of the connecting member makes it possible to use the same transfer device with cartridges of two different capacities.

After the liquid contained initially in the cartridge has been transferred to the inside of the bottle and it has been mixed with the lyophilisate, the mixture thus obtained is reaspirated into the cartridge 12 through the needle. For this purpose, the reservoir of the cartridge is pulled using the cap fixed to the needle support 202. When the mixture is transferred to the cartridge 12, the projections 232 slide along the slits 210 or 212. When the projections 232 come into contact with the end of these slits, the latter form an abutment and oppose subsequent displacement of the cartridge 12. Thus, any risk of the piston 34 being withdrawn from the reservoir of the cartridge on account of too great a displacement of the latter is avoided by the presence of the projections 232 forming an abutment. This is because these limit the course of displacement of the reservoir of the cartridge relative to the connecting member 24 secured to the piston.

What is claimed is:

1. A device for two-way transfer of a liquid (38) between a bottle (14), provided with a perforable stopper (44), and a cartridge (12), comprising a cylindrical reservoir (26) in which a perforable piston (34) slides, characterized in that it includes:

a body (16) having means for fixing to the bottle (14), a member (24) for connecting the perforable piston (34) to the body (16), a shuttle (20) which is displaceable relative to the body (16) and to said connecting member (24), the shuttle (20) bearing a hollow needle (22) of which a first end (112) is adapted to perforate the piston (34) and of which the second end (114) is adapted to perforate the stopper (44), and in that the shuttle (20) is displaceable between an initial position, in which the needle ends (112, 14) are spaced apart from the perforable piston (34) and the perforable stopper (44), and a final transfer position, in which the needle ends (112, 114) are received in the cartridge (12) and the bottle (14).

2. The device as claimed in claim 1, characterized in that said member (24) for connecting the piston to the body comprises means (96) for fixing to the body (16) and is movable relative to the body (16) from an initial position, in which the fixing means (96) are not in engagement with the body (16), and a final position, in which the fixing means (96, 98) are in engagement with the body, thus ensuring that the piston is connected to the body.

3. The device as claimed in claim 1, characterized in that said member (24) for connecting the piston to the body comprises a threaded protuberance (92) for fixing it in a tapped recess (36) in the piston (34).

4. The device as claimed in claim 1, characterized in that said shuttle (20) is mounted so as to slide in a conduit (91) of said member (24) for connecting the piston to the body.

5. The device as claimed in claim 4, characterized in that said conduit (91) has on the inside an abutment (100) limiting the displacement travel of the shuttle (20).

6. The device as claimed in claim 1, characterized in that it comprises a protective cap (18) initially mounted on the body (16), which protective cap (18) has means (80) for fixing it to the reservoir (26) of the cartridge.

7. The device as claimed in claim 1, characterized in that the body (16) has a continuation surrounding said shuttle (20) and extending beyond the first end (112) of the needle.

8. The device as claimed in claim 1, characterized in that it comprises at least one abutment (232) limiting the axial displacement of the reservoir (26) relative to the connecting member (24), preventing removal of the piston (34) from the reservoir (26).

9. The device as claimed in claim 8, characterized in that it comprises a cartridge support (202) on which the reservoir (26) of the cartridge (12) bears axially, and in that one of the cartridge support (202) and connecting member (24) has at least one projection, forming said abutment (232), received in a longitudinal slit (210, 212) of the other of the cartridge support (202) and connecting member (24), in order to limit their relative axial displacement between the reservoir (26) and the connecting member (24).

10. An injection kit including a device (10) for two-way transfer according to claim 1, and a cartridge (12) and a bottle (14), in which the cartridge (12) is initially connected to the connecting member (24) and the bottle (14) is initially connected to the body (16).

* * * * *